US009619875B2

United States Patent
Rooney et al.

(10) Patent No.: US 9,619,875 B2
(45) Date of Patent: Apr. 11, 2017

(54) CONTRAST REAGENT LEAKAGE CORRECTION IN DYNAMIC SUSCEPTIBILITY CONTRAST MAGNETIC RESONANCE IMAGING

(71) Applicants: William Rooney, Lake Oswego, OR (US); Xin Li, Beaverton, OR (US)

(72) Inventors: William Rooney, Lake Oswego, OR (US); Xin Li, Beaverton, OR (US)

(73) Assignee: OREGON HEALTH & SCIENCE UNIVERSITY, Portland, OR (US)

(*) Notice: Subject to any disclaimer, the term of this patent is extended or adjusted under 35 U.S.C. 154(b) by 0 days.

(21) Appl. No.: 14/694,319

(22) Filed: Apr. 23, 2015

(65) Prior Publication Data
US 2015/0310598 A1    Oct. 29, 2015

Related U.S. Application Data

(60) Provisional application No. 61/983,905, filed on Apr. 24, 2014.

(51) Int. Cl.
*G06K 9/00* (2006.01)
*G06T 7/00* (2017.01)
*A61K 49/10* (2006.01)

(52) U.S. Cl.
CPC .............. *G06T 7/00* (2013.01); *A61K 49/106* (2013.01); *G06T 7/0016* (2013.01); *G06T 2200/04* (2013.01); *G06T 2207/10088* (2013.01); *G06T 2207/10096* (2013.01); *G06T 2207/30016* (2013.01); *G06T 2207/30096* (2013.01); *G06T 2207/30104* (2013.01)

(58) Field of Classification Search
None
See application file for complete search history.

(56) References Cited

U.S. PATENT DOCUMENTS

| 8,718,747 | B2* | 5/2014 | Bjornerud | A61B 5/055 |
| | | | | 382/128 |
| 2006/0034765 | A1* | 2/2006 | Schmainda | A61K 49/06 |
| | | | | 424/9.3 |
| 2009/0104123 | A1* | 4/2009 | Yang | A61K 49/0002 |
| | | | | 424/9.3 |
| 2010/0296714 | A1* | 11/2010 | Schmainda | A61B 5/0263 |
| | | | | 382/131 |
| 2011/0201917 | A1* | 8/2011 | Li | A61B 5/055 |
| | | | | 600/410 |

* cited by examiner

*Primary Examiner* — Shervin Nakhjavan
(74) *Attorney, Agent, or Firm* — Jeffrey M. Jackson

(57) ABSTRACT

Disclosed are methods and systems for calculating a contrast reagent (CR) extravasation rate constant and generating a contrast reagent leakage corrected relative cerebral blood volume (rCBV) image map of a brain region from dynamic susceptibility contrast (DSC) magnetic resonance imaging (MRI) time-course image data based on pharmacokinetic first principles. In one example approach, a computerized method may include performing a linearization transform of a DSC MRI time-course equation which accounts for an intravascular contribution and an extravasating component, and calculating CR leakage from a slope of a linear portion of the transformed data.

17 Claims, 4 Drawing Sheets 

CONTRAST REAGENT LEAKAGE CORRECTION IN DYNAMIC SUSCEPTIBILITY CONTRAST MAGNETIC RESONANCE IMAGING

ACKNOWLEDGMENT OF GOVERNMENT SUPPORT

This invention was made with government support under Grant Nos. RO1-CA137488 and R01-NS34608 awarded by The National Institutes of Health. The government has certain rights in the technology.

FIELD

The present disclosure relates to the field of Magnetic Resonance Imaging (MRI), and, more specifically, to dynamic susceptibility contrast (DSC) MRI for brain imaging.

BACKGROUND

Dynamic susceptibility contrast (DSC) Magnetic Resonance Imaging (MRI) is a technique of perfusion scanning using an MRI system wherein a contrast reagent (CR), such as a gadolinium-based contrast reagent (Gd CR), is injected and a time series of fast $T_2^*$-weighted images are acquired. DSC MRI with Gd CR has become one of the imaging standards for brain perfusion measurement and the depiction and detection of brain tumors.

Relative cerebral blood volume (rCBV) has been shown as a very useful imaging biomarker for brain tumor diagnosis, prognosis, and treatment/therapy response monitoring. Software packages like Nordic ICE 4 with Food and Drug Administration (FDA) 510 k clearance further illustrate the clinical relevance of rCBV. DSC MRI with low molecular weight Gd CR is often the method of choice for rCBV quantification.

However, DSC MRI with Gd CR is often confounded by CR leakage into brain tumor interstitium space, e.g., Gd CR leaks out of the vascular space when the blood brain barrier is compromised. Several model-based and model-independent leakage correction methods have been proposed. Examples of model-independent leakage correction approaches are described in Paulson E S and Schmainda K M, *Radiology* 249 601-613 (2008); and Emblem K E et al, *J Cereb Blood Flow Metab* 31, 2054-2064 (2011); both of which are incorporated by reference herein.

Using such approaches, pharmacokinetic indication of a corrected "leakage rate constant" remains to be clearly defined and the variable influence of the transient phase during CR first pass often further complicates rCBV calculations. In addition, effects of mixed $T_1/T_2^*$ weighting exhibited in the tails of DSC MRI time-courses are often subjected to further corrections thereby increasing computational time while providing inaccurate leakage correction results. Further, current FDA 510 k cleared packages for DSC MRI calculations provide options that either do not correct for Gd CR leaking into a brain lesion area or options that overcorrect Gd leakage. The result is a degraded diagnostic capacity of the DSC MRI. Thus, an optimal leakage correction approach remains to be properly identified for Gd CR.

SUMMARY

The present disclosure is directed to systems and methods for calculating a contrast reagent extravasation rate constant and generating a contrast reagent leakage corrected relative cerebral blood volume rCBV image map of a brain region from DSC MRI time-course image data. In one example, a computerized method may include performing a linearization transform of a DSC MRI time-course equation which accounts for an intravascular contribution and an extravasating component, and calculating Gd CR leakage from a slope of a linear portion of the transformed data.

The disclosed systems and methods identify the CR leakage rate and simplify rCBV quantification, thereby reducing calculation time while providing a more accurate and faster correction for Gd CR leakage for DSC-MRI when compared to other leakage correction methods. In particular, the disclosed systems and methods provide both a contrast reagent extravasation rate constant and an accurate rCBV map in a single DSC scan and a clear definition for Gd CR's pseudo leakage rate constant while reducing rCBV quantification to numerical integration and linear regression.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

Figure 1:
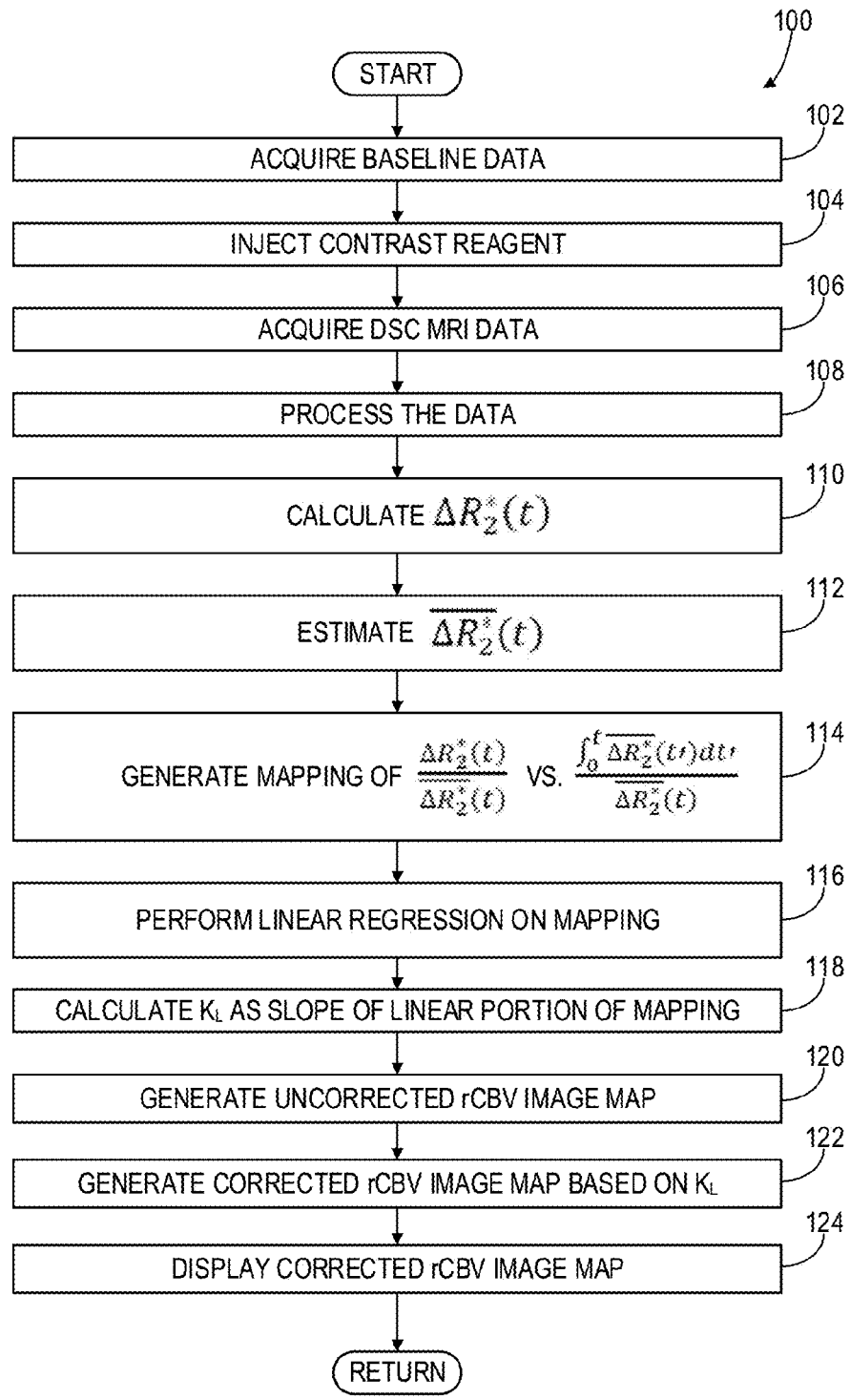
FIG. 1 shows an example method for contrast reagent leakage correction of DSC MRI time-course image data of a brain region, in accordance with the disclosure.

The following detailed description is directed to systems and methods of contrast reagent leakage correction of DSC MRI time-course image data of a brain region. In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents. Further, various operations may be described as multiple discrete operations in turn, in a manner that may be helpful in understanding embodiments; however, the order of description should not be construed to imply that these operations are order dependent.

As remarked above, DSC MRI with Gd CR has become one of the imaging standards for the depiction and detection of brain tumors and rCBV has been shown as a very useful imaging biomarker for brain tumor diagnosis, prognosis, and treatment response monitoring. Though previous model-based and model-independent leakage correction methods have been proposed, pharmacokinetic indication of the corrected CR leakage rate constant remains to be clearly defined and the variable influence of the transient phase during CR first pass often further complicates rCBV calculation. In addition, effects of mixed $T_1/T_2^*$ weighting particularly noticeable towards the tail of the DSC time-courses are often subjects of further corrections in previous approaches, thereby increasing computational time while providing inaccurate leakage correction results.

An example model-free approach is described in Boxerman J L et al, *AJNR Am J Neuroradiol*; 27, 859-867 (2006), which is hereby incorporated by reference in its entirety. To correct for CR leakage, such a model-free approach is based on the assumption that the extravasating and intravascular Gd introduced effective transverse relaxation rate constant ($R_2^*$) change can be linearly combined, so that the pixel $\Delta R_2^*(t)$ time-course accounting for an intravascular contribution and an extravasating component can be simplified to the following Equation 1:

$$\Delta R_2^*(t) \approx K_1 \overline{\Delta R_2^*}(t) - K_2 \int_0^t \overline{\Delta R_2^*}(t') dt' \qquad (Eq. 1)$$

In Equation 1, $\Delta R_2^*(t)$ represents the pixel time-course for $R_2^*$ change, and $K_1$ and $K_2$ are proportional constants for intravascular and extravasating contributions to $\Delta R_2^*(t)$, respectively. $\overline{\Delta R_2^*}(t)$ is an effective transverse relaxation rate constant for relative blood which may be calculated as the time-course of $R_2^*$ change from all non-leaking pixels available within the imaging slice or volume. Following the basic DSC assumption that $\Delta R_2^*(t)$ change is proportional to blood volume fraction, $\overline{\Delta R_2^*}(t)$ represents a simple and robust way to estimate relative blood $\Delta R_2^*$ time-course. The negative sign in Equation 1 reflects the MRI specific phenomenon that CR-introduced $T_1$ shortening will cause a signal increase post CR, opposing that of signal reduction in a heavily $T_2^*$-weighted DSC sequence.

Due to temporal resolution and signal-to-noise ratio (SNR) requirements, DSC measurements are typically carried out in a mixed $T_1/T_2^*$ weighting, thus both of the time dependent tissue relaxation time constants ($T_1$ and $T_2^*$) contribute to changes in DSC signal intensity time-course. With extravasating CR, the susceptibility gradient across the blood vessel will also be reduced due to CR extravasation and this causes a reduced $R_2^*$ difference between blood and tissue. Since it is also related to extravasation, this reduced $R_2^*$ difference also affects the extravasating term, the integration term with $K_2$ constant in Equation 1, resulting in $K_2$ itself being either positive or negative. Thus, $K_2$ is not a commonly defined pharmacokinetic rate constant, but a potential pseudo rate constant that reflects MRI signal weighting from CR extravasation. Nevertheless, if $K_2$ is a pseudo first-order rate constant reflecting CR extravasation, its value and pharmacokinetic meaning can still be well identified through pharmacokinetic first principles. Performing a linearization transform of Equation 1 yields the following Equation 2:

$$\frac{\Delta R_2^*(t)}{\overline{\Delta R_2^*}(t)} = K_1 - K_L \frac{\int_0^t \overline{\Delta R_2^*}(t') dt'}{\overline{\Delta R_2^*}(t)} \qquad (Eq. 2)$$

In Equation 2, $K_L$, representing a pseudo first-order leakage rate constant, is used to differentiate it from $K_2$. The significance of the difference between $K_L$ and $K_2$ is described in more detail below. From Equation 2, if the $\Delta R_2^*(t)/\overline{\Delta R_2^*}(t)$ term is graphed as the ordinate with the $\int_0^t \overline{\Delta R_2^*}(t')dt'/\overline{\Delta R_2^*}(t)$ term as the abscissa, fundamental pharmacokinetic theorem predicts that for $K_L$ to be a true pseudo first order rate constant associated with Gd extravasation, then after the system reaches Gd transport equilibrium, there will be a linear portion within the graph, with its slope being the Gd CR transfer constant which is the desired leakage rate constant $K_L$. In addition, since Equation 1 ignores CR intravasation, a computational linear analysis approach (e.g., a linear regression) may be applied to a linearization graph based on Equation 2 to automatically detect a starting point where the graphed data deviates from the linear portion. For example, such a starting point may be identified in response to a linearity deviation above a predetermined threshold. Such a detected starting point may be utilized to identify a time point where the influence of intravasation increases above a threshold.

FIG. 1 shows an example method 100 for contrast reagent leakage correction of DSC MRI time-course image data of a brain region. For example, method 100 may be used to calculate a contrast reagent extravasation rate constant ($K_L$) and generate a contrast reagent leakage corrected rCBV image map of a brain region from DSC MRI time-course image data based on pharmacokinetic first principles. One or more steps of method 100 may be performed by one or more computing devices, such as the computing device described below with regard to FIG. 5. Such computing devices may comprise an MRI data acquisition system, one or more processors included in an MRI system, one or more image processors, and/or any other suitable processors which include physical circuitry programmed to automatically perform steps of method 100. It should be understood that the various acts illustrated in method 100 may be performed in the sequence illustrated, in other sequences, in parallel, or in some cases omitted. In some examples, a contrast reagent injection may be performed prior to performing method 100. However, a contrast reagent injection performed prior to method 100, often termed a preload dose, would not affect the various acts of method 100 described below.

At 102, method 100 includes acquiring baseline data. For example, an image processor may be utilized to acquire DSC MRI time-course image data for a region of interest of a brain of a patient prior to an injection of a contrast reagent to obtain a baseline signal intensity. Any number of DSC MRI imaging volumes over any suitable duration may be acquired prior to an injection of a contrast reagent, e.g., 7 imaging volumes may be acquired over a period of 11 seconds, so that a baseline signal intensity may be calculated from the data. The baseline signal intensity may be calculated form the baseline data in any suitable manner, e.g., the baseline signal intensity may be computed as an average of the baseline signal data. In some examples, the baseline data may be predetermined and stored in a memory component of a computing device.

At 104, method 100 includes injecting a contrast reagent into a blood vessel which induces a differential between the susceptibilities of the blood vessel and a region of interest in the brain. Any suitable contrast reagent may be used; e.g., the contrast reagent may comprise a gadolinium-based contrast reagent. Injecting a contrast reagent may comprise injecting a bolus of suitable contrast reagent intravenously into a blood vessel of the patient in any suitable way; e.g., by utilizing a power injector. Following injection of the contrast reagent a saline flush may be injected into the blood vessel.

At 106, method 100 includes acquiring DSC MRI data. For example, an image processor may be utilized to acquire DSC MRI time-course image data for the region of interest following the injection of the contrast reagent into the blood vessel. Acquiring DSC MRI time-course image data for the region of interest may comprises acquiring any suitable number of dynamic $T_2^*$-weighted images of the region of interest using any suitable gradient-echo echo planar imaging pulse sequence with a predetermined repetition time, echo time, flip angle, file of view, and imaging matrix.

At 108, method 100 may include processing the DSC MRI time-course image data. For example, the DSC MRI time-course image data may be motion corrected within the dynamic DSC MRI time-course series using any suitable image registration or motion correction approach. A suitable processor may be utilized to perform any other suitable processing of the DSC MRI time-course image data to prepare the data for computational analysis, e.g., to perform filtering, noise reduction, etc.

At 110, method 100 includes calculating a pixel time-course of an effective transverse relaxation rate constant change ($\Delta R_2^*(t)$) from the DSC MRI image data series. In particular, for at least one pixel or voxel in the DSC MRI time-course image data, $\Delta R_2^*(t)$ may be computed based on the baseline signal intensity and an imaging echo time of a pulse sequence used to acquire the DSC MRI data. For example, $\Delta R_2^*(t)$ may be calculated according to the following Equation 3:

$$\Delta R_2^*(t) = -\frac{\ln\left(\frac{S(t)}{S_0}\right)}{TE} \qquad \text{(Eq. 3)}$$

In Equation 3, $S(t)$ is the DSC MRI pixel image at time t, $S_0$ is the baseline signal intensity, and TE is the imaging echo time.

At 112, method 100 includes computing an estimate of a time-course of an effective transverse relaxation rate constant for relative blood ($\overline{\Delta R_2^*}(t)$) from the DSC MRI time-course image data. $\overline{\Delta R_2^*}(t)$ may be computed based on a combination of signal changes from non-leaking pixels within the DSC MRI time-course image data. To define non-leaking pixels, a threshold method can be implemented. First, $R_2^*$ time-course of individual pixels within the brain can be calculated. Then the standard deviation (SD) of $R_2^*$ from the tail of the time-courses of all pixels can be calculated. Those pixels that don't show an elevated time-course tail above 1 SD can be selected as non-leaking voxels. In some examples, thresholds other than 1 SD may be used. $\overline{\Delta R_2^*}(t)$ can then be calculated from the combined signal of all non-leaking pixels.

At 114, method 100 includes generating a mapping of $\Delta R_2^*(t)/\overline{\Delta R_2^*}(t)$ versus $\int_0^t \overline{\Delta R_2^*}(t')dt'/\overline{\Delta R_2^*}(t)$. For example, a processor may be utilized to graph the $\Delta R_2^*(t)/\overline{\Delta R_2^*}(t)$ term of Equation 2 as the ordinate (y-axis) with $\int_0^t \overline{\Delta R_2^*}(t')dt'/\overline{\Delta R_2^*}(t)$ as the abscissa (x-axis). This mapping may be stored in a memory component of a computing device so that the data in the mapping may be further processed as described below.

At 116, method 100 includes performing a linear regression on a linear portion of the mapping of $\Delta R_2^*(t)/\overline{\Delta R_2^*}(t)$ versus $\int_0^t \overline{\Delta R_2^*}/\overline{\Delta R_2^*}(t')dt'/\overline{\Delta R_2^*}(t)$. For example, a processor may be utilized to identify a linear portion of the mapping data and perform linear regression of the mapping data. The linear portion of the mapping may correspond to DSC MRI time-course image data acquired following a transient period of contrast reagent first pass. In some examples, the linear portion of the mapping may correspond to DSC MRI time-course image data acquired from a predetermined starting time point following injection of the contrast reagent to a predetermined ending time point following injection of the contrast reagent. For example, the linear portion of the mapping may correspond to DSC MRI time-course image data acquired from approximately 40 seconds after injection of the contrast reagent to approximately 70 seconds after injection of the contrast reagent. Additionally, in some examples, an intravasation period may be identified from the mapping in response to a deviation from linearity in the mapping following the transient period of contrast reagent first pass.

At 118, method 100 includes calculating a contrast reagent extravasating rate constant ($K_L$) from the slope of the linear portion of the mapping. For example, $K_L$ may be computed based on a slope determined from the linear regression performed on the linear portion of the time-course.

At 120, method 100 may include generating an uncorrected rCBV image map. For example, a processor may be utilized to perform a numerical integration of $\Delta R_2^*(t)$ over the DSC MRI time-course image data for each pixel in the region of interest to generate an image map of relative cerebral blood volume (rCBV) in the region of interest.

At 122, method 100 may include generating a corrected rCBV map based on the contrast reagent extravasating rate constant ($K_L$). For example, a processor may be utilized to generate a corrected rCBV image map to correct the rCBV image map obtained in step 120 for leakage of the contrast reagent out of the patient's vasculature based on the contrast reagent extravasating rate constant. As an example, generating a corrected rCBV image map may performed according to the following Equation 4:

$$rCBV_{LC} = rCBV_{un} + K_L \int_0^T dt' \int_0^{t'} \overline{\Delta R_2^*}(t)dt \qquad \text{(Eq. 4)}$$

In Equation 4, $rCBV_{LC}$ is the leakage corrected rCBV, $rCBV_{un}$ is uncorrected rCBV, and $K_L$ is the contrast reagent extravasating rate constant.

At 124, method 100 may include displaying the corrected rCBV image map. For example, a processor may be utilized to output the contrast leakage corrected rCBV image map to a suitable display device. The corrected rCBV image map may be output in any suitable format to any suitable device and, in some examples, the rCBV image map may be stored in a memory component of a computing device. Additionally, the corrected rCBV image map may be used for brain tumor diagnosis, prognosis, and treatment/therapy response monitoring. For example, rCBV values for the region of interest may be compared against predetermined threshold values to inform a diagnosis and to guide treatment.

EXAMPLE

The following example demonstrates the leakage correction method described above with regard to FIG. 1. In this example, intravascular ferumoxytol DSC MRI data was used as a control to validate computations of contrast reagent extravasation rate constants and contrast reagent leakage corrected rCBV image maps for Gd CR DSC MRI data. As remarked above, the leakage correction approach described herein uniquely identifies the CR leakage rate and significantly simplifies rCBV quantification thereby reducing calculation time while providing a more accurate and faster correction for Gd CR leakage for DSC-MRI when compared to previous leakage correction approaches. The approach described herein further clarifies that only one correction step is necessary and thus potentially paves a pathway for investigating CR pre-loading dose on DSC leakage rate quantification.

In this example, extracellular Gd (~600 Da) contrast reagent and the high-molecular weight (750 kDa) iron-based intravascular ferumoxytol (Fe) were used to demonstrate the efficacy of the linearization approach described above with regard to FIG. 1, and show that such an approach resolves several issues in DSC quantification when extravasating CR is used. In particular, such an approach may be used to uniquely identify an extravasation rate constant, to effectively minimize leakage correction steps, and to understand pre-loading dose (an additional CR injection before the DSC acquisition commencement) on leakage rate and rCBV quantification.

Data Collection

In this example, 17 subjects with Glioblastoma multiforme (GBM) were prospectively studied on institutional review board approved protocols. Informed written consent was obtained from each subject. Subjects underwent MRI sessions consisting of two consecutive days of MRI scans. On the first day, pre- and post-contrast $T_1$-weighted images and DSC-MRI were acquired using gadoteridol gadolinium (III) chelate (ProHance, Bracco Diagnostic Inc., Princeton, N.J.). On the following day, the same MRI sequences were acquired using ferumoxytol (provided by AMAG Pharmaceuticals, Inc., Cambridge, Mass.). No subject had any complications during the MR examinations. All MRI sessions were conducted using a 3T whole-body MRI system (TIM TRIO, Siemens, Erlangen, Germany) with a body coil for RF transmitting and a 12-channel matrix head coil for signal receiving.

For DSC-MRI, dynamic $T_2^*$-weighted images were acquired using a gradient-echo echo planar imaging pulse sequence (repetition time 1500 ms, echo time 20 ms, flip angle 45°, field of view 192×192 mm, matrix 64×64, and 27 interleaved slices). After an initial baseline period of seven imaging volumes (11 s), a rapid bolus of contrast reagent (Gd or Fe) was administered intravenously using a power injector (Spectris Solaris—MEDRAD Inc., Warrendale, Pa.) through an 18-gauge intravenous line at a rate of 3 mL/s, followed immediately by 20 mL of saline flush at the same rate. Including baseline, DSC data were collected up to 90 volumes (frames). Gadoteridol was injected at a dose of 0.1 mmol/kg of body weight. Ferumoxytol was given as a dose of either 1 mg/kg, 2 mg/kg, or in a constant volume of 2.5 mL diluted with 2.5 mL saline (75 mg) regardless of body weight.

Imaging Analysis

All Gd and Fe DSC data were first motion corrected within each dynamic series and then between the series using FMRIB's Linear Image Registration Tool (FLIRT) within FM RIB Software Library (FSL). Data processing was performed using in-house software written in Matlab (Mathworks, Natick, Mass.). The approach described above with regard to Equation 3 was used to calculate $\Delta R_2^*(t)$. The Gd CR extravasating rate constant was calculated either with the Equation 1 fitting approach to obtain $K_2$, or the $K_L$ constant defined as the slope of the linear portion of the graphed points using Equation 2. In this example, linear regression was performed starting at 40 seconds post CR injection to ensure minimal influence of CR transient period (period (i) shown in in FIGS. 2E and 2F described below) on $K_L$ quantification. Leakage corrected rCBV was calculated from the following Equation 5:

$$rCBV_{LC} = rCBV_{un} + K_{2,L} \int_0^T dt \int_0^t \overline{\Delta R_2^*}(t) dt \quad (Eq. 5)$$

In Equation 5, $rCBV_{LC}$ is the leakage corrected rCBV, $rCBV_{un}$ is that for uncorrected rCBV, and $K_{2,L}$ takes either the $K_2$ or $K_L$ leakage rate to correct for CR extravasation. The last term of Equation 5 estimates integrated $\Delta R_2^*$ introduced by CR extravasation. This example showed that the CR extravasating rate constant is more accurate and uniquely estimated with $K_L$ compared to estimates using $K_2$. Additionally, as described below, $K_L$ has a clear pharmacokinetic interpretation whereas $K_2$ does not.

Results

Figure 2:
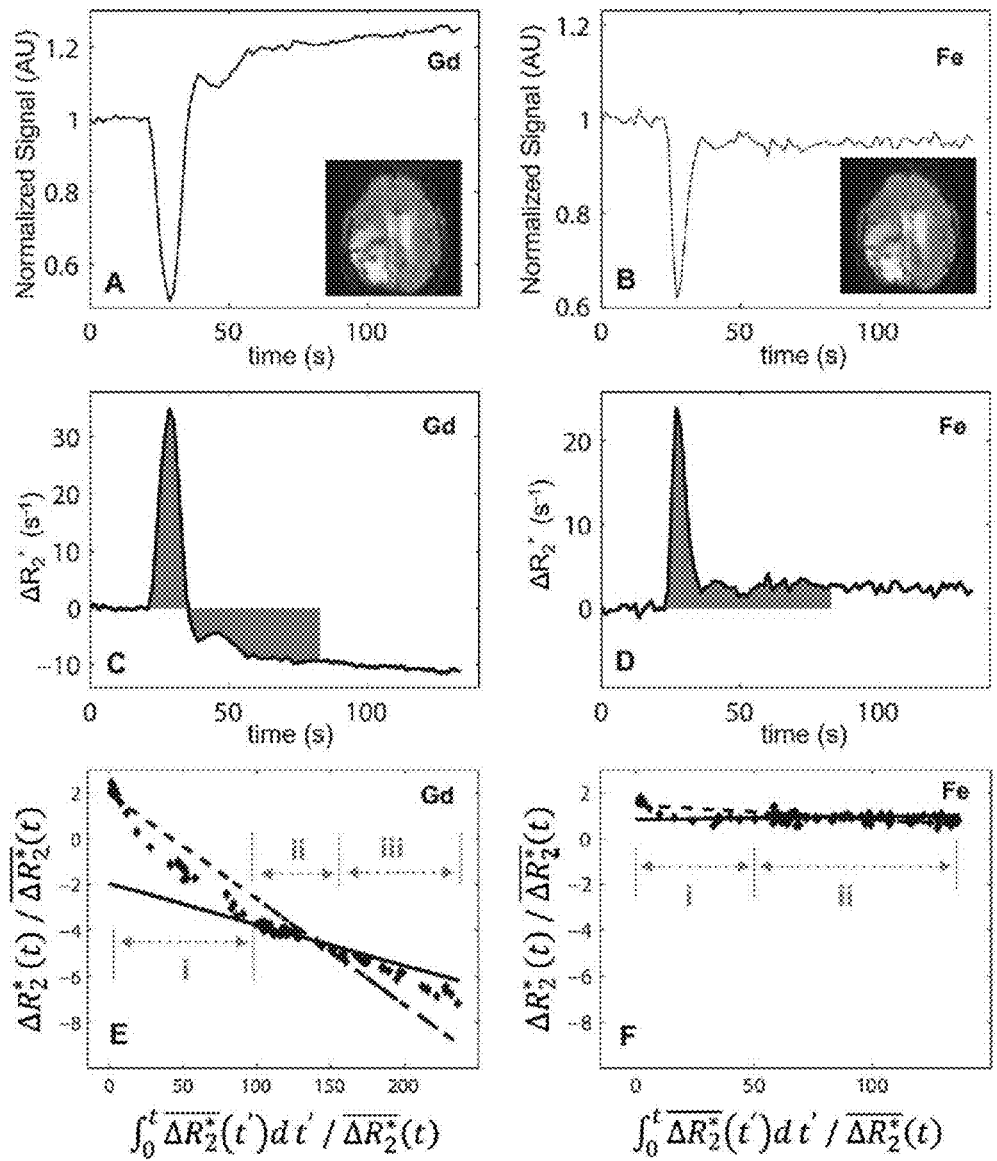
FIG. 2 shows example DSC MRI time-courses and associated CR leakage rate quantification in accordance with the disclosure.

FIG. 2 shows example time-courses in DSC MRI and associated leakage rate quantification for extracellular or intravascular CRs. In particular, representative co-registered pixel intensity time-courses from enhancing lesion area for Gd and Fe CRs are shown in FIGS. 2A and 2B, respectively. Insets in FIGS. 2A and 2B display corresponding same frame co-registered post-injection dynamic images. While the time-course shown in FIG. 2B exhibits a consistent signal reduction post Fe as expected in the predominately $T_2^*$-weighted DSC sequence, the signature "leakage effect" of the signal to increase above the baseline due to $T_1$ shortening post Gd is evident in FIG. 2A. With a direct calculation of $\Delta R_2^*$ (described above with regard to Equation 3), the change of $R_2^*$ time-course artificially dips below zero after CR first pass (FIG. 2C). The shaded area illustrates that numerical integration of $\Delta R_2^*$ underestimates the rCBV value. In particular, integration of the $\Delta R_2^*$ time-course up to ~1.0 minute post injection resulted in an underestimation of rCBV values due to partial cancellation of the positive and negative shaded areas as well as underestimation of the positive peak, as illustrated in FIG. 2C. For the nano-sized intravascular Fe CR, $\Delta R_2^* > 0$ at all times throughout the CR passage and this returned consistent rCBV estimation as illustrated in FIG. 2D.

As described above, one approach in leakage correction is to use Equation 1 to estimate a leakage rate constant by fitting post Gd CR data points with both $K_1$ and $K_2$ as fitting parameters. Such an approach is based on CR's influence throughout its passage. However, one drawback of this approach is that CR's influence at different time points post CR injection may not be effectively summarized with the Equation 1 approach. The CR transient phase during Gd CR first pass and CR intravasation after a certain time post CR injection are two primary issues that are not well covered by the Equation 1 approach. In fact, previous efforts to model CR mean transient time (MTT) while keeping DSC acquisition short are representative considerations in dealing with these issues.

FIG. 2E symbols show the same pixel data from FIG. 2A that underwent the Equation 2 linearization transform and plotted with respective coordinates as labeled. The solid line with a slope of $K_L$ is from a linear regression of the transformed data points with abscissa numerical range from 100 to 140 on FIG. 2E abscissa scale, reflecting a DSC time-course range from 40 s to 70 s post-CR injection. The dashed line has a slope of $K_2$ determined from fitting Equation 1 post CR points, which involves all data points up to 70 s post CR injection. The plot can be roughly divided into three periods: i) transient period of CR first pass; ii) pseudo equilibrium period where linearity obtains; and iii) intravasation/linearity deviation period, where data clearly deviate from period ii linear trend, most likely due to CR intravasation. In the data used in this example, it was extremely rare (<<0.1%) to observe pixels with appreciable linearity departure (period iii) in Gd CR data when using the FIG. 2E approach, even though post CR $T_1$ shortening caused signal increases above the baseline like that shown in FIG. 2A is common. This indicates intravasation may not be a noticeable confounder for DSC with less than 70 s post CR injection data. With no measurable CR extravasation, the linear transformed plot of the intravascular Fe CR in FIG. 2F showed no departure from the linear trend even towards the end of the DSC time course (no appreciable Fe intravasation when there is no Fe in interstitium space). For the Fe data of the same pixel only periods (i) and (ii) were definable.

Figure 3:
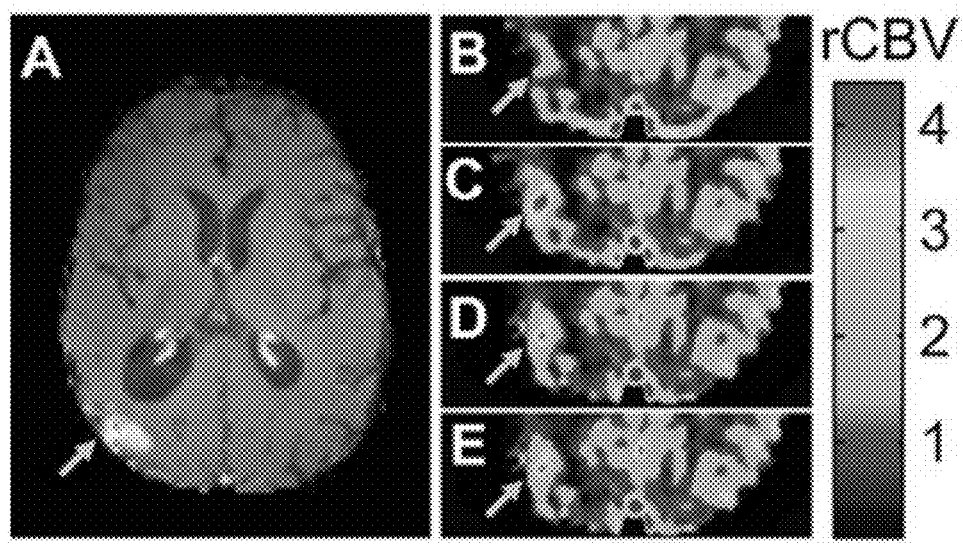
FIG. 3 shows an example $T_1$ weighted image slice post CR injection and example rCBV image maps with and without CR leakage correction.

To demonstrate the spatial correlation of the current approach, FIG. 3A shows a $T_1$-weighted image slice post Gd injection. An enhancing lesion is indicated with the arrow. FIGS. 3B-3E show rCBV maps zoomed to the bottom part of the FIG. 3A brain slice. In particular, FIG. 3B shows a Gd rCBV map without leakage correction; FIG. 3C shows a leakage corrected Gd rCBV map, where leakage correction was performed using leakage rate $K_2$ derived from fitting Equation 1; FIG. 3D shows a leakage corrected rCBV with a leakage rate constant of $K_L$, the slope of the linear portion of the Equation 2 transformed data; and FIG. 3E shows an Fe rCBV map. Compared with FIG. 3E, rCBV in the lesion area (arrow) is generally underestimated without leakage correction (FIG. 3B) and was overestimated using the Equation 1 fitting approach (FIG. 3C). With leakage rate constant clearly defined as $K_L$, FIG. 3D represents the best agreement between Fe and leakage corrected Gd rCBV maps.

Figure 4:
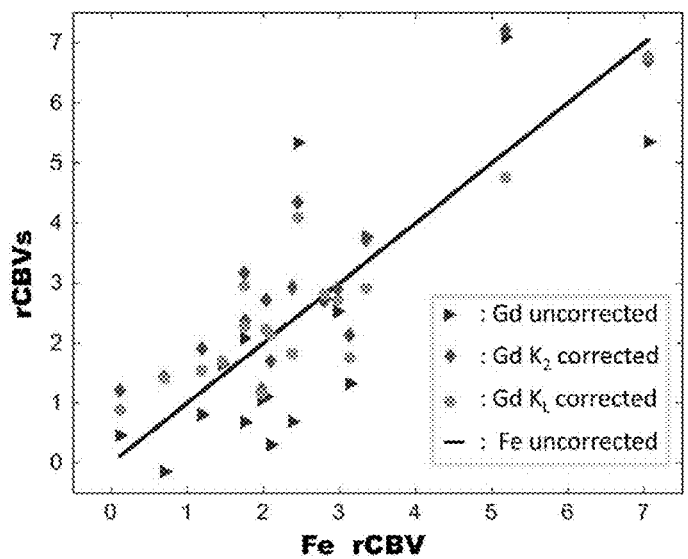
FIG. 4 shows an example plot of rCBV values with and without leakage correction against control rCBV values.

FIG. 4 shows a plot of the three Gd rCBVs vs. Fe rCBVs (solid line) for lesion regions of interest (ROIs) of all 17 subjects included in the study: Gd without leakage correction (▶); with Equation 1 fitted $K_2$ leakage correction (♦); and with $K_L$, the slope of the linear portion of the Equation 2 graph, leakage correction (●). Compared to Fe rCBV, the uncorrected Gd rCBVs underestimate and the $K_2$ corrected rCBV often overestimate. The relatively more evenly distributed rCBV with $K_L$ correction around the solid line empirically demonstrate its superior performance.

This example demonstrates the efficacy of the $K_L$ approach described herein to correct for brain lesion Gd CR leakage in DSC MRI using concepts from pharmacokinetic first principles. Such an approach provides a clear pseudo first order CR leakage rate constant even under mixed $T_1/T_2^*$ signal weighting, removing concerns on ambiguity in the $K_2$ rate constant definition. This example further demonstrates that a DSC signal time-course tail consistently staying below the baseline does not alone provide definitive evidence for leakage (FIG. 2B). In contrast to previous approaches, this $K_L$ approach demonstrates that leakage correction only need one step and that a DSC time course tail not returning to the baseline is not an indicator for further correction. This approach applies pharmacokinetic first principles to a non-pharmacokinetic expression that accounts for MRI signal weighting, provides insight for DSC data quantification, and enables the correction procedure to obtain $K_L$ with proper pharmacokinetic implications: under the transformed graph, data before entering the linear portion defines the influence of CR transient phase while data points departing the linear trend towards the tail of the time-course reflects intravasation.

Since MTT values are predominantly determined to be less than 8 seconds for a healthy brain or high grade glioma, a 40 second window is normally more than sufficient for any transit period to complete. For brain tumors, appreciable CR intravasation normally cannot be observed at 70 s post CR injection. Thus, in this example, the DSC time window was adopted to be from 40 to 70 seconds post-CR for the $K_L$ calculation. In addition, with this selected range, linear transformed data points affected by the transit effect were systematically positioned on one side of the linear trend (FIGS. 2E and 2F) and thus a deviation can be identified using numerical approaches. Further, even in lesion areas with significant Gd CR leakage, most linearization transformed data showed a pattern similar to that of FIG. 2F with no obvious linearity departure towards the end of DSC scan, except the noticeably larger slope in absolute value.

It has been shown that a pre-loading dose can be a practical way to minimize CR leakage effect in DSC. Based on this linearization transformation approach, $K_L$ can be similarly identified with a pre-loading dose and its magnitude is expected to be CR pre-loading dose dependent. However, uniquely quantifying $K_L$ each time provides a platform for investigating DSC parameter dependence on pre-loading dose systematically.

The current example demonstrates that the $K_L$ approach described herein provides a model-free CR leakage correction method that is faster and easier compared to model-dependent alternatives and thus can provide robust and rapid DSC MRI quantification for translational research as well as clinical applications.

In some embodiments, the above described methods and processes may be tied to a computing system, including one or more computers. In particular, the methods and processes described herein, e.g., method 100 described above, may be implemented as a computer application, computer service, computer API, computer library, and/or other computer program product.

Figure 5:
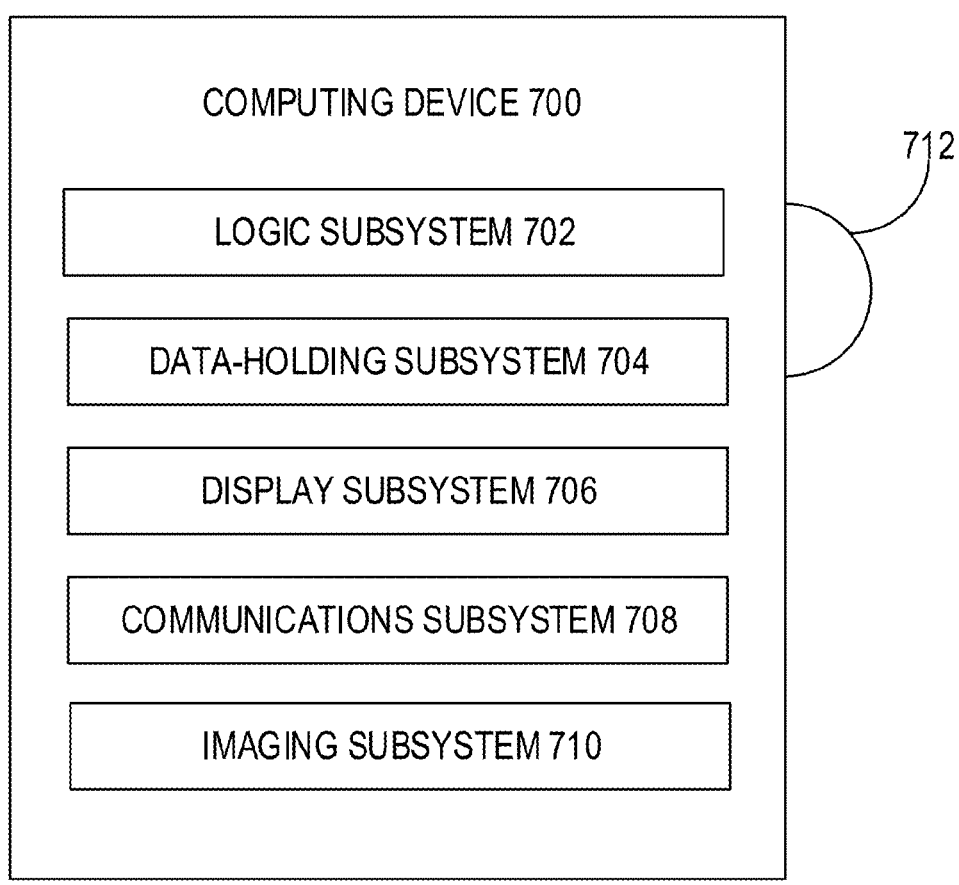
FIG. 5 schematically shows an example computing system in accordance with the disclosure.

FIG. 5 schematically shows a non-limiting computing device 500 that may perform one or more of the above described methods and processes. For example, FIG. 5 may represent an MRI data acquisition system, an image processing system, and/or any suitable processor which includes circuitry programmed to perform the various operations described herein. Computing device 500 is shown in simplified form. It is to be understood that virtually any computer architecture may be used without departing from the scope of this disclosure. In different embodiments, computing device 500 may take the form of a microcomputer, an integrated computer circuit, microchip, a mainframe computer, server computer, desktop computer, laptop computer, tablet computer, home entertainment computer, network computing device, mobile computing device, mobile communication device, gaming device, etc.

Computing device 500 includes a logic subsystem 502 and a data-holding subsystem 504. Computing device 500 may optionally include a display subsystem 506 and a communication subsystem 508, and/or other components not shown in FIG. 5. Computing device 500 may also optionally include user input devices such as manually actuated buttons, switches, keyboards, mice, game controllers, cameras, microphones, and/or touch screens, for example.

Logic subsystem 502 may include one or more physical devices configured to execute one or more machine-readable instructions. For example, the logic subsystem may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

The logic subsystem may include one or more processors that are configured to execute software instructions. Additionally or alternatively, the logic subsystem may include one or more hardware or firmware logic machines configured to execute hardware or firmware instructions. Processors of the logic subsystem may be single core or multicore, and the programs executed thereon may be configured for parallel or distributed processing. The logic subsystem may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration.

Data-holding subsystem 504 may include one or more physical, non-transitory devices configured to hold data and/or instructions executable by the logic subsystem to implement the herein described methods and processes. When such methods and processes are implemented, the state of data-holding subsystem 504 may be transformed (e.g., to hold different data).

Data-holding subsystem 504 may include removable media and/or built-in devices. Data-holding subsystem 504 may include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 504 may include devices with one or more of the following characteristics: volatile, nonvolatile, dynamic, static, read/write, read-only, random access, sequential access, location addressable, file addressable, and content addressable. In some embodiments, logic subsystem 502 and data-holding subsystem 504 may be integrated into one or more common devices, such as an application specific integrated circuit or a system on a chip.

FIG. 5 also shows an aspect of the data-holding subsystem in the form of removable computer-readable storage media 512, which may be used to store and/or transfer data and/or instructions executable to implement the herein described methods and processes. Removable computer-readable storage media 512 may take the form of CDs, DVDs, HD-DVDs, Blu-Ray Discs, EEPROMs, flash memory cards, and/or floppy disks, among others.

When included, display subsystem 506 may be used to present a visual representation of data held by data-holding subsystem 504. As the herein described methods and processes change the data held by the data-holding subsystem, and thus transform the state of the data-holding subsystem, the state of display subsystem 506 may likewise be transformed to visually represent changes in the underlying data. Display subsystem 506 may include one or more display devices utilizing virtually any type of technology. Such display devices may be combined with logic subsystem 502 and/or data-holding subsystem 504 in a shared enclosure, or such display devices may be peripheral display devices. In some embodiments, computing device 500 may additionally include an audio subsystem including one or more speakers which may be used to present audio representations of data held by data-holding subsystem 504.

When included, imaging subsystem 506 may be used acquire and/or process any suitable image data from various sensors or imaging devices in communication with computing device 500. For example, imaging subsystem may be configured to acquire MRI data as part of an MRI system. Imaging subsystem 506 may be combined with logic subsystem 502 and/or data-holding subsystem 504 in a shared enclosure, or such imaging subsystems may comprise periphery imaging devices. Data received from the imaging subsystem may be held by data-holding subsystem 504.

When included, communication subsystem 508 may be configured to communicatively couple computing device 500 with one or more other computing devices. Communication subsystem 508 may include wired and/or wireless communication devices compatible with one or more different communication protocols. As non-limiting examples, the communication subsystem may be configured for communication via a wireless telephone network, a wireless local area network, a wired local area network, a wireless wide area network, a wired wide area network, etc. In some embodiments, the communication subsystem may allow computing device 500 to send and/or receive messages to and/or from other devices via a network such as the Internet.

It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the above-described processes may be changed.

The subject matter of the present disclosure includes all novel and non-obvious combinations and subcombinations of the various processes, systems and configurations, and other features, functions, acts, and/or properties disclosed herein, as well as any and all equivalents thereof.

The invention claimed is:

1. A computerized method for contrast reagent leakage correction of dynamic susceptibility contrast (DSC) magnetic resonance imaging (MRI) time-course image data of a brain region, the method comprising:
   from the DSC MRI time-course image data, computing a pixel time-course of an effective transverse relaxation rate constant change ($\Delta R_2^*(t)$) and an estimate of a time-course of an effective transverse relaxation rate constant change for relative blood ($\overline{\Delta R_2^*}(t)$);
   computing a contrast reagent extravasating rate constant ($K_L$) from a slope of a linear portion of a mapping of $\Delta R_2^*(t)/\overline{\Delta R_2^*}(t)$ versus $\int_0^t \Delta R_2^*(t')dt'/\Delta R_2^*(t)$;
   generating a relative cerebral blood volume (rCBV) image map;
   generating a contrast reagent leakage corrected relative cerebral blood volume ($rCBV_{LC}$) image map based on the contrast reagent extravasating rate constant ($K_L$),
   wherein the contrast reagent leakage corrected $rCBV_{LC}$ image map is generated using the equation:

$$rCBV_{LC} = rCBV_{un} + K_L \int_0^T dt' \int_0^{t'} \overline{\Delta R_2^*}(t) dt$$

where $rCBV_{LC}$ is the leakage-corrected rCBV, $rCBV_{un}$ is uncorrected rCBV, $K_L$ is the contrast reagent extravasating rate constant, and $\overline{\Delta R_2^*}(t)$ is the effective transverse relaxation rate constant change for relative blood.

2. The method of claim 1, wherein the contrast reagent comprises a gadolinium-based contrast reagent.

3. The method of claim 1, wherein the linear portion of the mapping corresponds to DSC MRI time-course image data acquired following a transient period of contrast reagent first pass.

4. The method of claim 1, wherein $\Delta R_2^*(t)$ is computed based on a baseline signal intensity and an imaging echo time of a pulse sequence used to acquire the DSC MRI data.

5. The method of claim 1, wherein $\overline{\Delta R_2^*}(t)$ is computed based on a combination of signal changes from non-leaking pixels within the DSC MRI time-course image data.

6. The method of claim 1, wherein the DSC MRI time-course image data comprises dynamic $T_2^*$-weighted images of the brain region acquired using a gradient-echo echo planar imaging pulse sequence.

7. The method of claim 1, wherein $\Delta R_2^*(t)$ is computed according to the equation:

$$\Delta R_2^*(t) = -\frac{\ln\left(\frac{S(t)}{S_0}\right)}{TE}$$

where $S(t)$ is the DSC MRI pixel image at time t, $S_0$ is a baseline signal intensity, and TE is an imaging echo time of a pulse sequence used to acquire the DSC MRI data.

8. The method of claim 1, wherein the linear portion of the mapping corresponds to DSC MRI time-course image data acquired from approximately 40 seconds after injection of the contrast reagent to approximately 70 seconds after injection of the contrast reagent.

9. A method for producing an image of a patient's brain with a magnetic resonance imaging (MRI) system, comprising:
  acquiring dynamic susceptibility contrast (DSC) MRI time-course image data for a region of interest of the brain prior to an injection of a contrast reagent to obtain a baseline signal intensity;
  acquiring DSC MRI time-course image data for the region of interest following an injection of a contrast reagent into a blood vessel which induces a differential between the susceptibilities of the blood vessel and tissue in the region of interest;
  from the DSC MRI time-course image data, calculating a pixel time-course of an effective transverse relaxation rate constant change ($\Delta R_2^*(t)$) based on the baseline signal intensity and an imaging echo time of a pulse sequence used to acquire the DSC MRI data;
  calculating an estimate of a time-course of an effective transverse relaxation rate constant change for relative blood ($\overline{\Delta R_2^*}(t)$) based on a combination of signal changes from non-leaking pixels within the DSC MRI time-course image data;
  calculating a contrast reagent extravasating rate constant ($K_L$) from a slope of a linear portion of a mapping of $\Delta R_2^*(t)/\overline{\Delta R_2^*}(t)$ versus $\int_0^t \overline{\Delta R_2^*}(t')dt'/\overline{\Delta R_2^*}(t)$, where the linear portion of the mapping corresponds to DSC MRI time-course image data acquire following a transient period of contrast reagent first pass;
  generating an image map of relative cerebral blood volume (rCBV) in the region of interest based on an integration of $\Delta R_2^*(t)$ over the DSC MRI time-course image data for each pixel in the region of interest;
  generating a corrected rCBV image map to correct the rCBV image map for leakage of the contrast reagent out of the patient's vasculature based on the contrast reagent extravasating rate constant ($K_L$); and
  outputting the corrected rCBV image map to a display device.

10. The method of claim 9, wherein the contrast reagent comprises a gadolinium-based contrast reagent.

11. The method of claim 9, wherein acquiring DSC MRI time-course image data for the region of interest comprises acquiring dynamic $T_2^*$-weighted images of the region of interest using a gradient-echo echo planar imaging pulse sequence.

12. The method of claim 9, wherein $\Delta R_2^*(t)$ is calculated according to the equation:

$$\Delta R_2^*(t) = -\frac{\ln\left(\frac{S(t)}{S_0}\right)}{TE}$$

where $S(t)$ is the DSC MRI pixel image at time t, $S_0$ is the baseline signal intensity, and TE is the imaging echo time.

13. The method of claim 9, wherein the linear portion of the mapping corresponds to DSC MRI time-course image data acquired from approximately 40 seconds after injection of the contrast reagent to approximately 70 seconds after injection of the contrast reagent.

14. The method of claim 9, wherein the corrected rCBV image map is generated according to the equation:

$$rCBV_{LC} = rCBV_{un} + K_L \int_0^T dt' \int_0^{t'} \overline{\Delta R_2^*}(t)dt$$

where $rCBV_{LC}$ is the leakage corrected rCBV, $rCBV_{un}$ is uncorrected rCBV, $K_L$ is the contrast reagent extravasating rate constant, and $\overline{\Delta R_2^*}(t)$ is the effective transverse relaxation rate constant change for relative blood.

15. The method of claim 9, further comprising motion correcting the DSC MRI time-course image data.

16. The method or claim 9, further comprising performing a linear regression on the linear portion of the mapping to obtain the contrast reagent extravasating rate constant.

17. The method of claim 9, further comprising identifying an intravasation period from the mapping in response to a deviation from linearity in the mapping following the transient period of contrast reagent first pass.

* * * * *

UNITED STATES PATENT AND TRADEMARK OFFICE
CERTIFICATE OF CORRECTION

PATENT NO.        : 9,619,875 B2
APPLICATION NO.   : 14/694319
DATED             : April 11, 2017
INVENTOR(S)       : William Rooney It is certified that error appears in the above-identified patent and that said Letters Patent is hereby corrected as shown below:

In the Specification

Please delete the paragraph under the heading ACKNOWLEDGEMENT OF GOVERNMENT SUPPORT from Column 1, Line 8-11 that appears as:
"This invention was made with government support under Grant Nos. R01-CA137488 and R01-NS34608 awarded by The National Institutes of Health. The government has certain rights in the technology."

And replace it with the passage below:
-- This invention was made with government support under CA137488 and NS034608 awarded by the National Institutes of Health. The government has certain rights in the invention. --

Signed and Sealed this
Second Day of July, 2019

Andrei Iancu
*Director of the United States Patent and Trademark Office*